United States Patent
Tateyama

(10) Patent No.: US 9,939,414 B2
(45) Date of Patent: Apr. 10, 2018

(54) OBJECT INFORMATION ACQUIRING APPARATUS

(71) Applicant: CANON KABUSHIKI KAISHA, Tokyo (JP)

(72) Inventor: Jiro Tateyama, Yokohami (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 7 days.

(21) Appl. No.: 14/878,035

(22) Filed: Oct. 8, 2015

(65) Prior Publication Data

US 2016/0109415 A1 Apr. 21, 2016

(30) Foreign Application Priority Data

Oct. 17, 2014 (JP) ................................. 2014-213117

(51) Int. Cl.
| | |
|---|---|
| G01N 29/44 | (2006.01) |
| G01N 29/24 | (2006.01) |
| A61B 5/00 | (2006.01) |
| G01N 29/04 | (2006.01) |
| G01N 29/26 | (2006.01) |
| G01N 29/30 | (2006.01) |

(52) U.S. Cl.
CPC ....... *G01N 29/4463* (2013.01); *A61B 5/0095* (2013.01); *G01N 29/043* (2013.01); *G01N 29/2418* (2013.01); *G01N 29/262* (2013.01); *G01N 29/30* (2013.01)

(58) Field of Classification Search
CPC ................................................ G01N 29/4463
See application file for complete search history.

(56) References Cited

U.S. PATENT DOCUMENTS

| | | | |
|---|---|---|---|
| 2010/0249570 A1* | 9/2010 | Carson ................. | A61B 5/0059 600/407 |
| 2011/0230750 A1 | 9/2011 | Tateyama ...................... | 600/407 |
| 2013/0072798 A1 | 3/2013 | Tateyama ...................... | 600/444 |
| 2013/0312526 A1 | 11/2013 | Oishi .............................. | 73/620 |
| 2014/0098630 A1 | 4/2014 | Tateyama ........................ | 367/7 |
| 2014/0098639 A1 | 4/2014 | Tateyama ........................ | 367/7 |
| 2015/0090037 A1* | 4/2015 | Tokita .................. | A61B 5/0095 73/643 |
| 2015/0327771 A1* | 11/2015 | Baba .................... | A61B 5/0095 600/407 |
| 2016/0206246 A1* | 7/2016 | Baba .................... | A61B 5/0095 |
| 2016/0287085 A1* | 10/2016 | Fukui ................... | A61B 5/7203 |

FOREIGN PATENT DOCUMENTS

JP          2012-179348         9/2012

* cited by examiner

*Primary Examiner* — Ryan Walsh
(74) *Attorney, Agent, or Firm* — Fitzpatrick, Cella, Harper & Scinto

(57) ABSTRACT

An object information acquiring apparatus includes: a plurality of detecting elements each receiving an acoustic waves having propagated from an object irradiated with light and outputting an electrical signal; a probe that supports the plurality of detecting elements so that a high-resolution region in which directivity axes of at least part of the plurality of detecting elements converge is formed; a processor acquiring specific information on the object using the electrical signal; and a memory storing correction data for correcting the electrical signals output by the plurality of detecting elements, and used when the processor acquires the specific information.

24 Claims, 11 Drawing Sheets

| ELEMENT No. | GAIN (INITIAL) | DELAY [usec] (INITIAL) |
|---|---|---|
| 1 | × 1.13 | − 0.006 |
| 2 | × 1.21 | − 0.018 |
| ... | ... | ... |
| n | × 1.04 | + 0.010 |

OBJECT INFORMATION ACQUIRING APPARATUS

BACKGROUND OF THE INVENTION

Field of the Invention

The present invention relates to an object information acquiring apparatus.

Description of the Related Art

A general ultrasound diagnostic apparatus transmits ultrasound waves using a probe that includes a plurality of acoustic detecting elements and receives echo signals reflected from the boundary between tissues inside an object to thereby obtain morphological information on the inside of the object. By doing so, it is possible to detect a disease segment such as a tumor. In recent years, in order to further improve the efficiency of detecting disease segments, imaging of physiological information (that is, functional information) of an object is gathering attention. As means for imaging the functional information, photoacoustic tomography (PAT) which uses pulsed lights and photoacoustic waves has been proposed.

Photoacoustic tomography is a technique of imaging an inner tissue serving as a source of photoacoustic waves using a photoacoustic effect that, when an object is irradiated with pulsed lights generated from a light source, the photoacoustic waves (typically ultrasound waves) are generated by absorption of the beams having propagated and diffused inside the object. In photoacoustic tomography, a change with time in the photoacoustic waves received by acoustic detecting elements is detected at a plurality of positions to obtain signals, and the obtained signals are analyzed mathematically. This analysis is also referred to as reconstruction processing by which information related to optical characteristic values inside the object can be visualized three-dimensionally.

Japanese Patent Application Laid-open No. 2012-179348 discloses an apparatus including a hemispherical probe in which a plurality of acoustic detecting elements that receive photoacoustic waves from an object are provided so that the light-receiving surfaces thereof are at different angles. The apparatus further includes a scanning mechanism that moves the hemispherical probe in the XYZ-directions in order to move a relative position of a high-resolution region determined by an arrangement of the object and the hemispherical probe.

Patent Literature 1: Japanese Patent Application Laid-open No. 2012-179348

SUMMARY OF THE INVENTION

In a probe in which a plurality of acoustic detecting elements are disposed on a hemispherical light-receiving surface as in Japanese Patent Application Laid-open No. 2012-179348, when the accuracy of attachment of the elements to the hemispherical surface, the accuracy of the curvature of the hemispherical surface itself, or the like is insufficient, the sensitivity or phase of the signals received by the respective elements may vary. Thus, when the hemispherical probe is attached to the apparatus, initial calibration for calculating correction values (correction data) for correcting a variation in the sensitivity or phase is required.

That is, if the angles and distances between a central position of a hemispherical surface and respective elements attached to the hemispherical surface are equal, the phases or sensitivities of the signals that the respective elements receive when a point sound source is installed at the central position of the hemispherical surface will be equal. Thus, when initial calibration is performed, a black point which is a light absorber having a high optical absorption coefficient and serves as a point sound source is installed at the central position of the hemispherical surface. Moreover, using photoacoustic waves generated when the black point is irradiated with pulsed lights, a variation in the sensitivity and phase of the signals received by the respective elements is calculated to create correction data.

Moreover, in the hemispherical probe, a high-resolution region is formed near the central point on which the high reception sensitivity directions of the respective elements converge. Thus, by providing a scanning mechanism that moves the hemispherical probe in the XYZ-directions, it is possible to move the high-resolution region inside the object to cover the entire imaging area of the object.

Here, since the piezoelectric characteristics deteriorate when an electric field is repeatedly applied to PZT (lead zirconate titanate) commonly used in acoustic detecting elements, the sensitivity varies due to the aging. Further, the accuracy of the positions of the respective elements attached to the hemispherical surface varies due to the aging. Thus, it is necessary to calculate an offset amount from the initial correction data (at the time of shipping from a factory, for example) indicating the central position of the hemispherical surface by measuring an aging state of the acoustic detecting elements during a maintenance operation performed as startup checking whenever the apparatus starts.

In view of the above problems, it is an object of the present invention to facilitate calibration of a probe in relation to acoustic detecting elements in an apparatus that acquires information on an object using photoacoustic tomography.

The present invention provides an object information acquiring apparatus comprising:
 a plurality of detecting elements configured to receive an acoustic wave having propagated from an object irradiated with light and output an electrical signal respectively;
 a probe configured to support the plurality of detecting elements so that a high-resolution region in which directivity axes of at least part of the plurality of detecting elements converge is formed;
 a processor configured to acquire specific information on the object using the electrical signal; and
 a memory configured to store correction data for correcting the electrical signals output by the plurality of detecting elements, and used when the processor acquires the specific information, the correction data including information based on a position of each of the plurality of detecting elements and information based on sensitivity, wherein
 the processor revises the correction data on the basis of the electrical signals output by the plurality of detecting elements when a light absorber for calibration disposed at a predetermined position in relation to the probe is used as the object during calibration of the object information acquiring apparatus.

According to the aspects of the present invention, it is possible to facilitate calibration of a probe in relation to acoustic detecting elements in an apparatus that acquires information on an object using photoacoustic tomography.

Further features of the present invention will become apparent from the following description of exemplary embodiments with reference to the attached drawings.

BRIEF DESCRIPTION OF THE DRAWINGS

FIG. 11 is a diagram illustrating an example of correction data stored in a memory.

DESCRIPTION OF THE EMBODIMENTS

Figure 1:
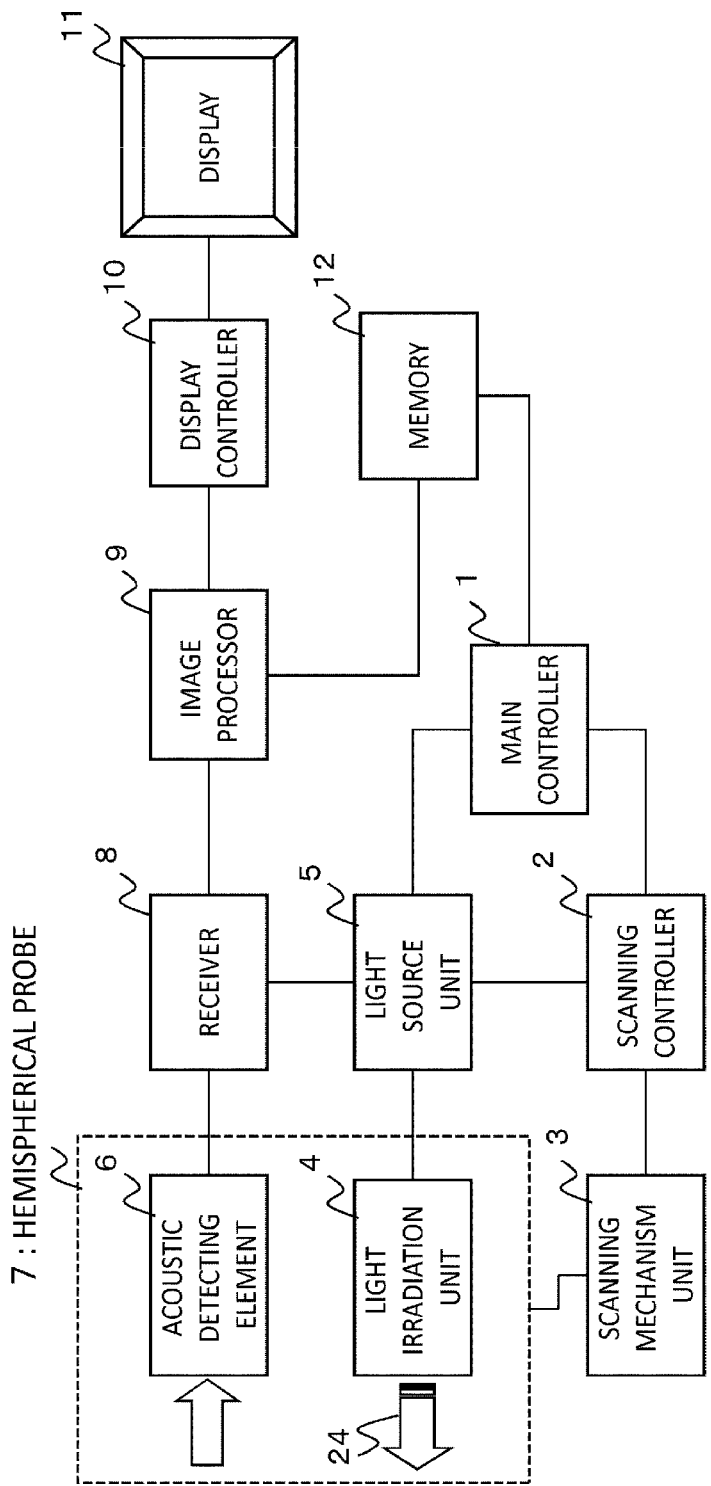
FIG. 1 is a diagram illustrating an entire configuration of an apparatus according to the present invention.

Hereinafter, preferred embodiments of the present invention will be described with reference to the drawings. Dimensions, materials, shapes, relative arrangements, and the like of constituent components described below are to be appropriately changed according to the configuration and various conditions of an apparatus to which the present invention is applied, and the scope of the present invention is not limited to those described below.

The present invention relates to a technique of detecting acoustic waves having propagated from an object to generate and acquire specific information on the interior of the object. Thus, the present invention can be understood as an object information acquiring apparatus or a control method thereof, and alternatively, as an object information acquiring method and a signal processing method. Moreover, the present invention can be understood as a program for allowing an information processing apparatus having hardware resources such as a CPU to execute these methods and a storage medium having the program stored therein. Further, the present invention can be understood as an acoustic wave measurement apparatus and a control method thereof.

The object information acquiring apparatus according to the present invention includes an apparatus which uses a photoacoustic tomography technique to irradiate an object with light (electromagnetic waves) to receive (detect) acoustic waves having propagated through the object after being generated inside or on the surface of the object according to a photoacoustic effect. Such an object information acquiring apparatus can be referred to as a photoacoustic imaging apparatus and a photoacoustic tomography apparatus in that specific information on the interior of the object is obtained in a format such as image data based on photoacoustic measurement.

The specific information in the photoacoustic apparatus indicates a generation source distribution of the acoustic waves generated by light irradiation, an initial sound pressure distribution inside the object, an optical energy absorption density distribution and an absorption coefficient distribution derived from the initial sound pressure distribution, or a concentration distribution of a substance that constitutes a tissue. Specific examples of the specific information include a blood component distribution such as oxygenated and reduced hemoglobin concentration distributions or an oxygen saturation distribution derived from the distributions, and a distribution of fats, collagen, and water. Moreover, the specific information may be obtained as distribution information at respective positions inside an object rather than as numerical data. That is, distribution information such as an absorption coefficient distribution or an oxygen saturation distribution may be used as object information.

Acoustic waves referred in the present invention are typically ultrasound waves, and include elastic waves called sound waves and acoustic waves. The acoustic waves generated by the photoacoustic effect are referred to as photoacoustic waves or light-induced ultrasound waves. Electrical signals converted from acoustic waves by a probe are also referred to as acoustic signals, and acoustic signals originating from photoacoustic waves are referred to as photoacoustic signals in particular.

The breast of a living body can be considered as an example of the object used in the present invention. The object is not limited thereto, and other segments of a living body and non-living materials can be also measured.

First Embodiment

FIG. 1 is a diagram illustrating an entire configuration of an object information acquiring apparatus which best illustrates the features of the present invention. A main controller 1 is the controller of the apparatus. A scanning controller 2 scans a probe 7 to a predetermined position. A scanning mechanism unit 3 mechanically moves the probe 7 according to the control of the scanning controller 2. A light irradiation unit 4 irradiates an object with light. A light source unit 5 controls the light irradiation unit 4. The scanning mechanism unit and the scanning controller may be referred to collectively as a scanner.

An acoustic detecting element 6 detects photoacoustic waves. The hemispherical probe 7 includes a plurality of acoustic detecting elements attached to a hemispherical support. A receiver 8 imports the reception signals detected by the acoustic detecting elements 6. An image processor 9 calculates image data using the reception signals of photoacoustic waves. A display controller 10 controls scan conversion of images and superimposed display. A display 11 displays image data. A memory 12 is formed of a nonvolatile memory, a magnetic medium, or the like and stores correction data for calibration. The memory is preferably a rewritable memory capable of rewriting stored correction data and storing changes in the correction data.

When specific information of an object is acquired to reconstruct an image, first, the light source unit 5 irradiates the object with pulsed lights using the light irradiation unit 4. Moreover, the acoustic detecting element 6 detects photoacoustic waves generated when biological tissues absorb the energy of the pulsed lights having propagated and diffused inside the object. Subsequently, the image processor 9 reconstructs the electrical signals (detection signals) originating from the photoacoustic waves as image data to acquire an optical characteristic distribution (in particular, an optical energy absorption density distribution) inside the object. That is, it is possible to visualize a "functional image" indicating a substance distribution of a biological tissue.

Figure 2:
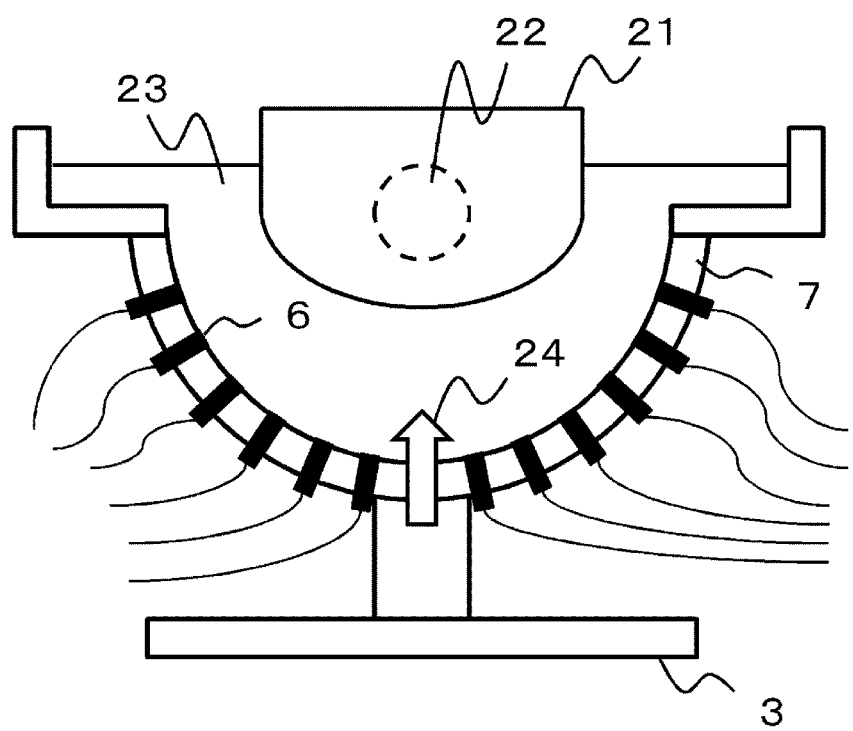
FIG. 2 is a diagram illustrating a configuration of a hemispherical probe.

FIG. 2 is a diagram for describing a configuration of the hemispherical probe 7. The plurality of acoustic detecting elements 6 are fixed to the hemispherical probe 7 of which the inner wall (the wall close to the object) has a hemispherical shape, and the light-receiving surfaces of the respective elements face the center of the hemispherical surface. In such an arrangement as illustrated in FIG. 2, in an image obtained by performing universal back-projection, the resolution is the highest at the center of the hemisphere and the resolution decreases proportionally to the distance from the center. Even when the plurality of acoustic detecting elements 6 are not disposed on a spherical surface, the high-resolution region is uniquely determined by the arrangement of the plurality of acoustic detecting elements 6.

Here, in the present embodiment, a high-resolution area near the central point serving as a high-resolution position is defined as a high-resolution region 22. The range of the high-resolution region 22 is determined depending on the tolerance for varied highest resolution. Thus, the range is determined depending on the required image accuracy and the apparatus performance. In other words, the high-resolution region is formed in the direction in which the high sensitivity directions (directivity axes) converge.

In actual measurement, preferably, an acoustic matching liquid 23 serving as a matching layer is filled inside the hemispherical probe 7 and an object 21 is placed in the liquid. The pulsed light 24 output from the light irradiation unit 4 is irradiated from the lower portion (pole) of the hemispherical probe 7 so as to reach the object. The hemispherical probe 7 is scanned by an XYZ-axis stage which is the scanning mechanism unit 3. In this way, a relative position of the object to the probe can be changed. By doing so, the high-resolution region 22 scans the entire object. In this case, in order to make the resolution uniform, it is preferable to scan the object in a direction in which the resolution is not uniform (that is, a direction in which the resolution has a gradient).

Figure 3:
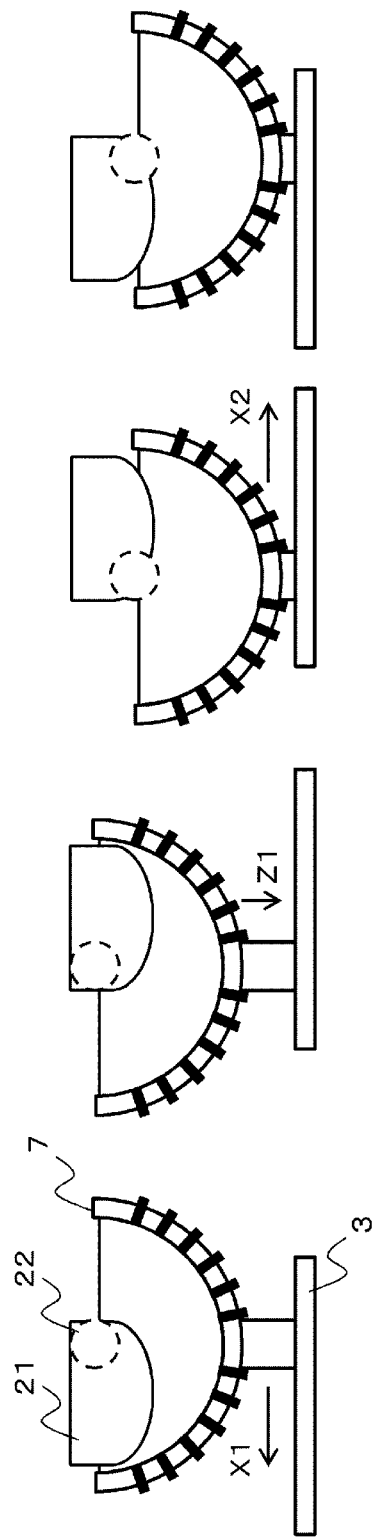
FIGS. 3A to 3D are diagrams illustrating a method of scanning the hemispherical probe.

FIG. 3 illustrates a specific method of scanning the hemispherical probe 7. FIG. 3A illustrates an initial position at which reception signals are acquired while scanning the hemispherical probe 7 in the direction X1 using the scanning stage 3. When the hemispherical probe 7 reaches the position illustrated in FIG. 3B, the hemispherical probe 7 is scanned in the direction Z1 to be positioned at the position illustrated in FIG. 3C. Subsequently, the hemispherical probe 7 is scanned in the direction X2 to acquire the reception signals until the hemispherical probe 7 reaches the position illustrated in FIG. 3D. This process is performed in an entire area of one plane (XZ-plane). After that, the position of the hemispherical probe 7 is shifted in a depth direction (Y-direction) and the same scanning and signal acquisition are repeatedly performed. In this way, scanning can be performed so that the high-resolution region 22 covers the entire area of the object 21.

Next, a measurement method according to the present embodiment will be described with reference to FIG. 4.

First, the light irradiation unit 4 irradiates the object 21 with a pulsed light 24 (S401). The acoustic detecting element 6 receives the photoacoustic waves excited by a light absorber inside the object according to the irradiated pulsed light and converts the photoacoustic waves to electrical signals and the receiver 7 imports the electrical signals (S402).

At the same time, the main controller 1 acquires scanning position information corresponding to the obtained reception signals from the scanning controller 2 to check a scanning range and determines whether the high-resolution region 22 has scanned an entire measurement area (S403). The entire measurement area is not limited to the entire object 21. That is, a measurement target area may be set arbitrarily according to an input from a user via a user interface and may be set to a predetermined range according to the apparatus design. When the scanning has not been completed, the hemispherical probe 7 is scanned (S404) to repeatedly perform irradiation of pulsed lights and acquisition of photoacoustic wave signals.

When scanning of the entire measurement range has been completed, the image processor 9 executes image reconstruction according to a universal back-projection method based on the obtained reception signals and the scanning position information (S405). In this case, the image processor 9 performs preprocessing such as differentiation and noise-filtering on the obtained reception signals and performs back-projection of allowing the processed signal to propagate in the opposite direction from the position of the acoustic detecting element 6. The image processor 9 performs the back-projection on the hemispherical probe at all scanning positions to superimpose the propagated processing signals. With this process, an information distribution inside the object such as an absorption coefficient distribution is acquired as image data. Finally, the image processor 9 outputs the obtained image data to the display controller 10 and displays an image on the display 11 (S406).

Figure 5:
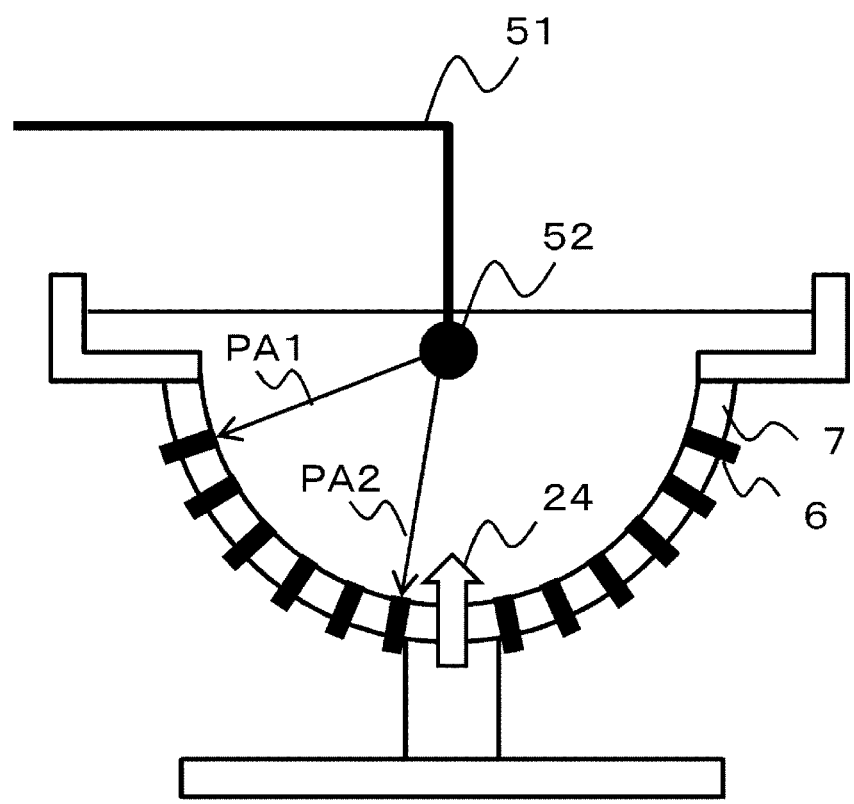
FIG. 5 is a diagram illustrating a method of calibrating the hemispherical probe.

FIG. 5 is a diagram illustrating a method of calibrating the plurality of acoustic detecting elements 6 attached to the hemispherical probe 7. First, using a fixing jig 51 that can fix an object to an optional coordinate position, a black point 52 as a light absorber for calibration is installed at the central position of the hemispherical probe 7. When the black point 52 is irradiated with the pulsed light 24, photoacoustic waves PA are generated from the black point 52 in a spherical form. In this case, if the black point 52 is installed correctly at the central position of the hemispherical surface, the photoacoustic waves PA reach the respective acoustic detecting elements 6 with the same signal strength and at the same phase time and are imported to the receiver as the reception signals.

Figure 6:
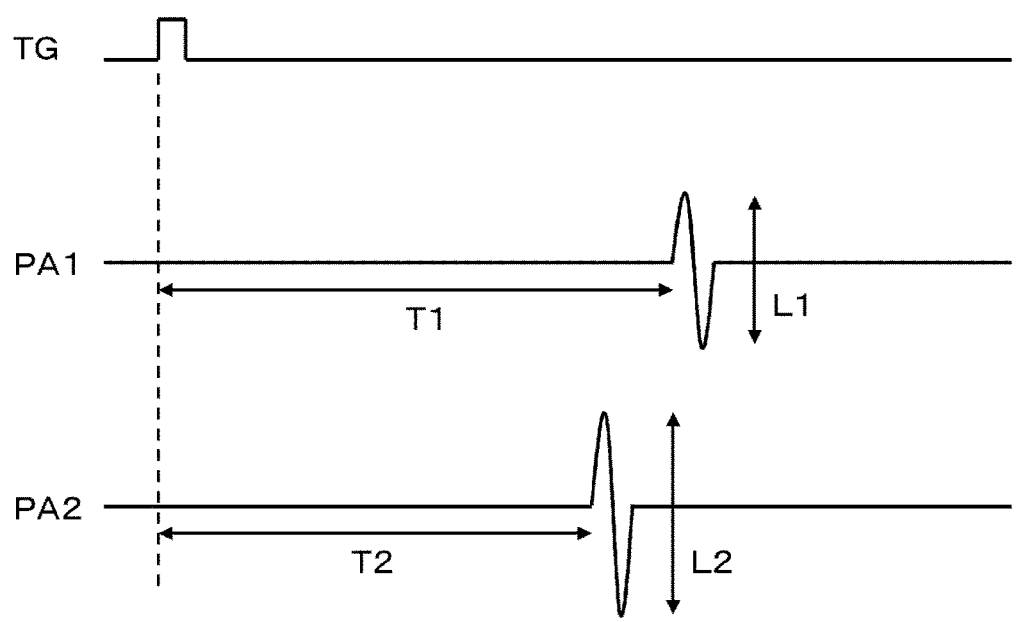
FIG. 6 is a timing chart illustrating the reception signals of photoacoustic waves.

FIG. 6 is a timing chart illustrating the irradiation of the pulsed light 24 and the delay and the signal strength of the received photoacoustic waves. The pulsed light 24 is irradiated at time TG. PA1 and PA2 indicate photoacoustic signals which have been generated from the black point 52 and arrived at different acoustic detecting elements 6-1 and 6-2. In FIG. 6, the arrival time T1 of PA1 is shorter than the arrival time T2 of PA2. Thus, it can be understood that the acoustic detecting element 6-2 is disposed closer to the black point 52 than the acoustic detecting element 6-1. Moreover, as for the signal strength, the amplitude L1 of PA1 is larger than the amplitude L2 of PA2.

Next, the cause of a shift in reception time (that is, a shift in the position from the hemisphere center) and a difference in the signal strength will be discussed. First, the difference in the signal strength is considered to be attributable to the fact that the respective elements are at different distances from the light absorber and thus, the degrees of attenuation are different. Further, a variation during manufacturing of piezoelectric elements such as PZT (lead zirconate titanate) commonly used as the acoustic detecting elements 6 can be considered as another cause of the difference in the signal strength. That is, since the signal conversion strength is different from element to element due to the variation during manufacturing, a sensitivity variation occurs. Further, the signal strength may vary due to a shift in the attitude angle of the acoustic detecting elements 6.

Moreover, the positional shift can be considered to be attributable to the fact that the accuracy of attachment of the acoustic detecting elements 6 to the hemispherical light-receiving surface, the accuracy of the curvature of the hemispherical surface itself, or the like is insufficient. Further, a deformation or a looseness of connecting portions during the use of the apparatus can be considered as another cause of the positional shift.

An image quality may decrease and artifacts may occur if image reconstruction is performed without taking into account a reception signal delay (a shift of the phase time from an intended value) and a change in the signal strength, which result from the positional shift of the respective elements and a sensitivity variation.

Thus, in an initial state when the hemispherical probe 7 is installed in the apparatus, it is necessary to perform calibration using the fixing jig and the black point 52 to measure the phase time and the signal strength of the respective elements in advance and to create variation correction data for each element. Specifically, the distance of each element from the black point and the reception sensitivity of each element are calculated based on a peak position and an amplitude of the electrical signal that each element of the probe outputs by receiving the photoacoustic wave and an acoustic velocity in the acoustic matching liquid. Moreover, the shifts in these values from the intended values when the apparatus was designed are calculated. That is, the correction data includes information based on the distance of each element from the hemisphere center and information based on the reception sensitivity of each element. The information based on the distance can be read information based on the position of each element and is typically relative position information of the high-resolution region to the element and arrival time information of the acoustic wave calculated from the relative position information.

The correction data is prepared for individual hemispherical probes 7. When the probe of the apparatus is replaced, the correction data is reacquired and updated. By doing so, it is possible to acquire stable reception signals which do not vary between apparatuses. Such creation of correction data performed at the startup of apparatuses is referred to as initial calibration. FIG. 11 illustrates an example of the correction data prepared for a certain probe. This correction data has a table format in which the delay (a shift from the design value of an apparatus) and the gain are stored for each element. By correcting the signals acquired by the respective elements according to this table, the signal strength and the reception time of an element can be made identical to those of the other elements.

However, the stored values are not limited to thereto. For example, a distance may be stored instead of the delay. In this example, although it is assumed that revision data for correction data is stored in addition to initial correction data (initial values), the correction data itself may be rewritten. Moreover, the calibration may be performed at any time other than the startup of an apparatus. For example, the calibration may be performed during periodic maintenance and may be performed at an optional time designated by a user. Moreover, instead of storing resultant information for correcting the electrical signal, the source data used for calculating such information may be stored.

Here, since the piezoelectric characteristics deteriorate when an electric field is repeatedly applied to a piezoelectric element formed of PZT (lead zirconate titanate) which is used in the acoustic detecting elements 6, the sensitivity varies due to the aging. Further, the attachment positions of the respective elements attached to the hemispherical surface vary due to the aging. Thus, it is necessary to measure an aging state of the acoustic detecting elements 6 during a maintenance operation of the apparatus. Such a maintenance operation may be performed whenever the apparatus starts and may be performed during periodic inspection. Based on the measured aging information, the correction data is updated and another correction data for the correction data is recorded.

However, the dedicated fixing jig 51 illustrated in FIG. 5 is necessary in order to fix the black point 52 at an accurate central position. As a result, since it is necessary to install the fixing jig 51 whenever a maintenance operation is performed, which is performed frequently, the operation is complicated.

Figure 7:
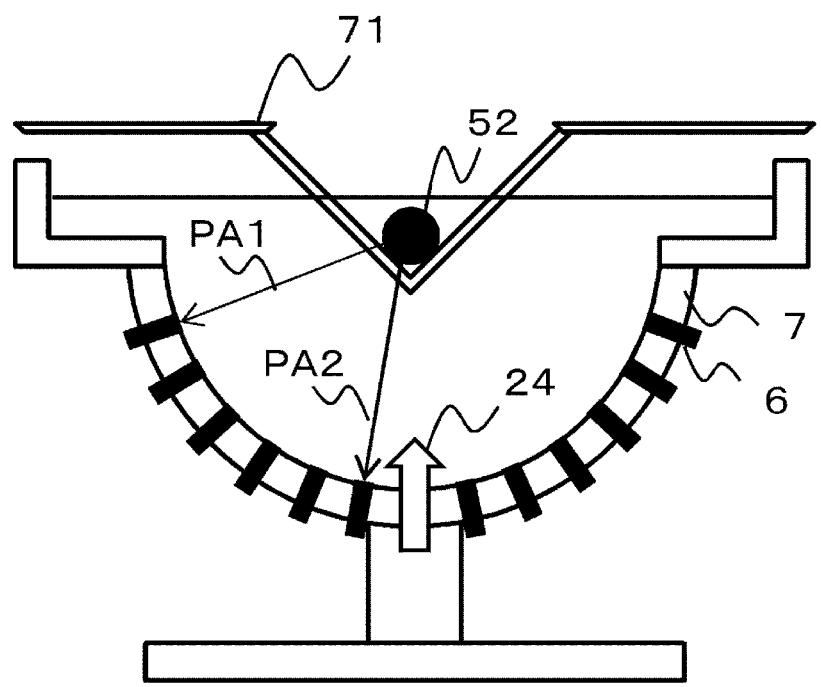
FIG. 7 is a diagram illustrating a method of fixing a black point.

FIG. 7 illustrates an example of a method of fixing the position of the black point 52 using a conical cup 71 as a fixing member to be substituted for the fixing jig 51. The shape of the cup 71 is not limited to the conical shape as long as it is possible to fix the position of the black point 52. For example, a depression may be formed in the lower end of the hemispherical surface. The cup 71 is preferably formed of a material which does not attenuate and refract the laser pulsed light 24 and the photoacoustic waves PA1 and PA2 having propagated through the acoustic matching liquid 23.

The fixing member is not limited to the cup 71 as long as the position of the black point 52 can be fixed easily. For example, a method of fixing the black point 52 using a wire or the like instead of the cup 71 and a structure in which the black point 52 is fixed by being embedded in a phantom formed of an acoustic matching material.

Figure 8:
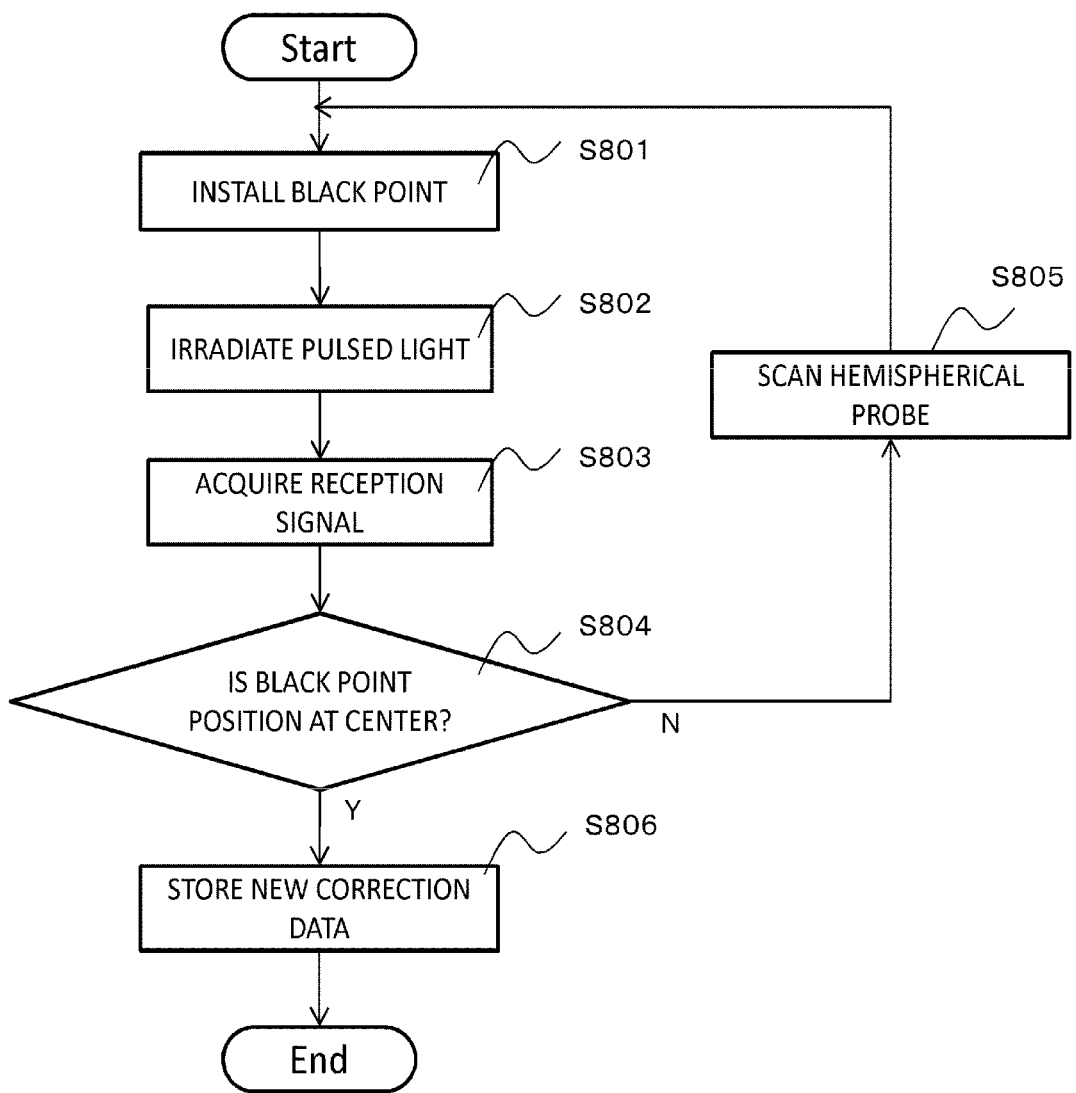
FIG. 8 is a flowchart illustrating a method of controlling a hemispherical probe according to a first embodiment.

FIG. 8 is a flowchart illustrating a control method of installing the black point 52 at the central position of the hemispherical probe 7 and scanning the hemispherical probe 7. That is, since the black point installed easily during a maintenance operation shifts from the central position of the hemispherical probe 7 whenever the maintenance operation is performed, it is necessary to perform control to seek a relative position of the black point 52 to the hemispherical probe 7.

In S801, the black point 52 is installed in a lower portion of the cup 71 and the position thereof is fixed. In S802, the light irradiation unit 4 irradiates a pulsed light 24. In S803, the photoacoustic waves PA generated from the black point 52 are detected by all acoustic detecting elements 6 to acquire reception signals.

S804 is a determination flow of detecting the phase time of the reception signals of the respective elements and calculating a relative position of the black point 52 to the center of the hemispherical probe 7. An example of the determination method will be described. First, a shape pattern such as an N-shaped spike which is highly likely to originate from photoacoustic waves is extracted from the reception signals and the signal strength is compared with a predetermined threshold to calculate an arrival time of the reception signal from the black point to the element. The distance between the element and the black point is calculated using the acoustic velocity in an acoustic matching liquid. This process is performed on the respective elements to obtain a relative position of the black point to the probe. Moreover, even when the position of some elements included in the probe shifts due to aging, the degree of the shift (the shifting direction and distance) is calculated by comparing the reception signals of the respective elements.

When it is determined in the determination flow of S804 that the black point 52 is not at the central position, the hemispherical probe 7 is scanned to correct the position in S805, and then, the processes starting with S801 are repeatedly performed. When the black point 52 matches the central position, an offset amount indicating the difference from the correction data in the initial calibration is calculated and is stored in the memory as new correction data in S806. In this case, the correction data itself may be updated and the offset amount may be stored as data for revising the correction data stored in advance.

Figure 4:
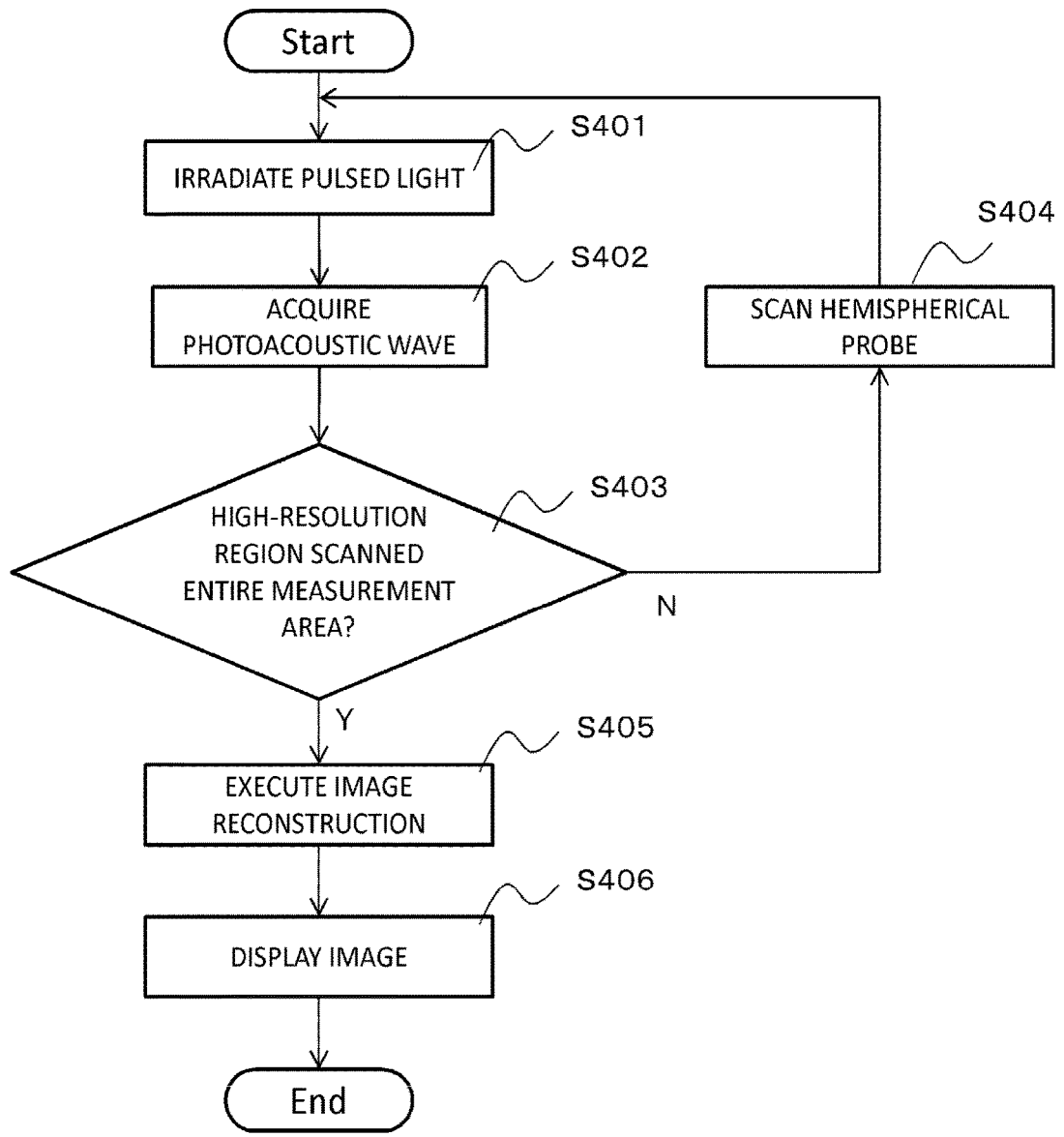
FIG. 4 is a flowchart illustrating a measurement method according to the present invention.

The correction data stored in the memory is used for image reconstruction illustrated in S405 of FIG. 4. That is, the image processor 9 applies a delay corresponding to the distance from the hemisphere center when reading the electrical signals received by the respective elements from the memory and applies a gain corresponding to the reception sensitivity when adding the electrical signals. By doing so, it is possible to correct the individual difference of the probes and to improve image accuracy. Further, in the present embodiment, since the updated correction data (or the revision data for the correction data) is used, it is possible to reconstruct an image by taking a change in the element sensitivity and a positional shift of the elements due to aging into account.

In the present embodiment, a method of correcting the reception signals during image reconstruction by calculating new correction data based on the signals (the phase difference between elements) from the respective elements has been described. In addition to applying a delay or gain to the reception signal itself, the correction data may be reflected on the weighting of each element during image reconstruction and the correction data may be reflected on image information processing.

Second Embodiment

In a second embodiment, a method of seeking a high-resolution position by moving the hemispherical probe in relation to a black point installed at an optional position during a maintenance operation performed whenever an apparatus starts and calculating an offset amount from an initial high-resolution position (initial setting position). It is assumed that the apparatus according to the second embodiment has the same configuration as that described above.

In the second embodiment, a correction offset amount indicates an offset amount of the position of the hemispherical probe. Moreover, correction data is used for correcting the scanning position of the hemispherical probe. Further, the correction offset amount is detected by a method of actually scanning the hemispherical probe to reconstruct an image of the black point, determining an image resolution, and detecting the range of the high-resolution region.

Figure 9:
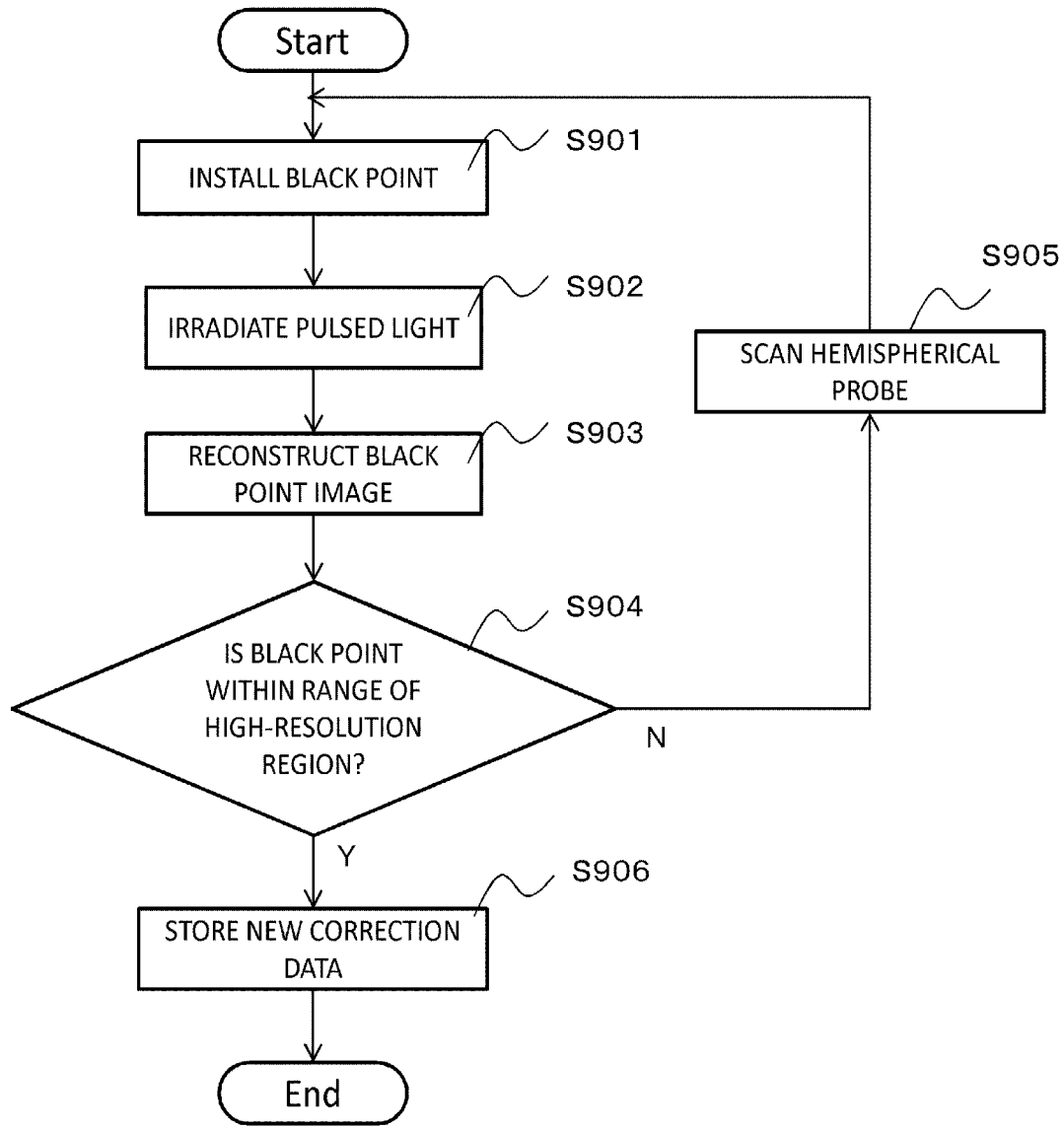
FIG. 9 is a flowchart illustrating a method of detecting a high-resolution region according to a second embodiment.

FIG. 9 is a flowchart illustrating a high-resolution region detecting method. In this flow, it is assumed that the black point 52 installed in a maintenance operation shifts from the central position of the hemispherical probe 7, and the relative position of the black point 52 to the hemispherical probe 7 is determined based on the resolution of the reconstructed image of the black point.

In S901, the black point 52 is installed in a lower portion of the cup 71 and the position thereof is fixed. The relative position at this time is defined as a first relation. In S902, the light irradiation unit 4 irradiates a pulsed light 24. In S903, the photoacoustic waves PA generated from the black point 52 are detected by all acoustic detecting elements 6 to acquire reception signals.

S904 is a determination flow of reconstructing an image of the black point from the reception signals of the respective elements and calculating a relative position indicating whether the black point 52 is within the range of the high-resolution region of the hemispherical probe 7. As a specific example, the image processor extracts a region originating from the black point from the reconstructed image using an existing image processing algorithm. Subsequently, the image processor determines whether an index value indicating the size, shape, signal strength, and the like of the region falls within a predetermined range obtainable when the black point is in the high-resolution region. In this case, it is more preferable to detect the shifting direction and the degree of the shift of the position of the high-resolution region and the black point. For example, when the actual black point is a sphere having a diameter of 0.5 mm and the black point in the reconstructed image is displayed as a sphere having a diameter of 1 mm, it is possible to determined whether the black point is in the high-resolution region by determining whether this diameter value falls within a predetermined allowable range.

When it is determined in S904 that the black point 52 is not in the high-resolution region, the scanning controller and the scanning mechanism unit scan the hemispherical probe 7 to correct the position in S905. In this way, the relative position changes from the first relation to a second relation. After that, the processes starting with S901 are repeatedly performed. The moving amount (distance and direction) at this time may be determined based on a predetermined unit amount and may be determined based on an offset amount of the black point position from the high-resolution region.

On the other hand, when the black point 52 is included in (or matches) the high-resolution region, the image processor calculates an offset amount indicating the difference from the scanning position during the initial calibration in S906. The memory stores the correction data updated based on the offset amount or revision data for the correction data.

As described above, in the present embodiment, in order to specify an actual high-resolution position, the black point is disposed at a predetermined setting position (an arbitrary position) to perform photoacoustic measurement and image reconstruction. Moreover, the probe is moved as necessary based on the resolution of the obtained black point image to seek a high-resolution position. In this way, it is possible to calculate an offset amount from a high-resolution position (initial setting value) determined by an apparatus configuration and the characteristics of individual probes and uses the offset amount as a correction value.

Modified Example

In the process flow described above, the probe is moved until an index value indicating the resolution of a reconstructed image falls within a predetermined threshold. Instead of this method, a method of repeating photoacoustic measurement and image reconstruction while gradually changing the relative position of the probe to the black point for a predetermined number of times (or for a predetermined period) may be used. In this case, the image processor compares a plurality of obtained reconstructed images to determine the position of the probe when the best image was obtained and updates the correction data for calibration based on the position. By applying a delay or gain to the reception signal using the correction data, it is possible to generate an image on which the actual element position and the reception sensitivity are reflected.

In the first and second embodiments, photoacoustic measurement is performed at a plurality of positions with scanning of the probe by the scanning mechanism unit and the scanning controller. However, it cannot be said that a scanning system is essential in implementation of the present invention. For example, photoacoustic measurement may be performed at respective positions while gradually moving the position of the black point manually or automatically and the reconstructed images obtained at the respective positions may be compared. In this case, it is preferably to provide such a stage mechanism capable of gradually moving the cup 71.

Further, it is not always necessary to perform photoacoustic measurement a plurality of number of times as long as it is possible to install a black point reliably at a high-resolution position at the time of shipping the apparatus. That is, the correction data according to the present invention can be updated as long as it is possible to compare the delay and strength of the actual reception signals acquired by the respective elements when the black point is at the high-resolution position with the initial design values of the apparatus. In this case, a high-accuracy black point installing machine is required.

Third Embodiment

In the first embodiment, the position information of the black point 52 is calculated based on the phase time of the reception signals. In the second embodiment, the offset amount between the installed position of the black point and the high-resolution position is calculated based on the reconstructed image. In a third embodiment, a method of calculating and correcting a variation in the amplitude of the reception signals associated with a sensitivity variation due to aging of the individual acoustic detecting elements 6 will be described.

Figure 10:
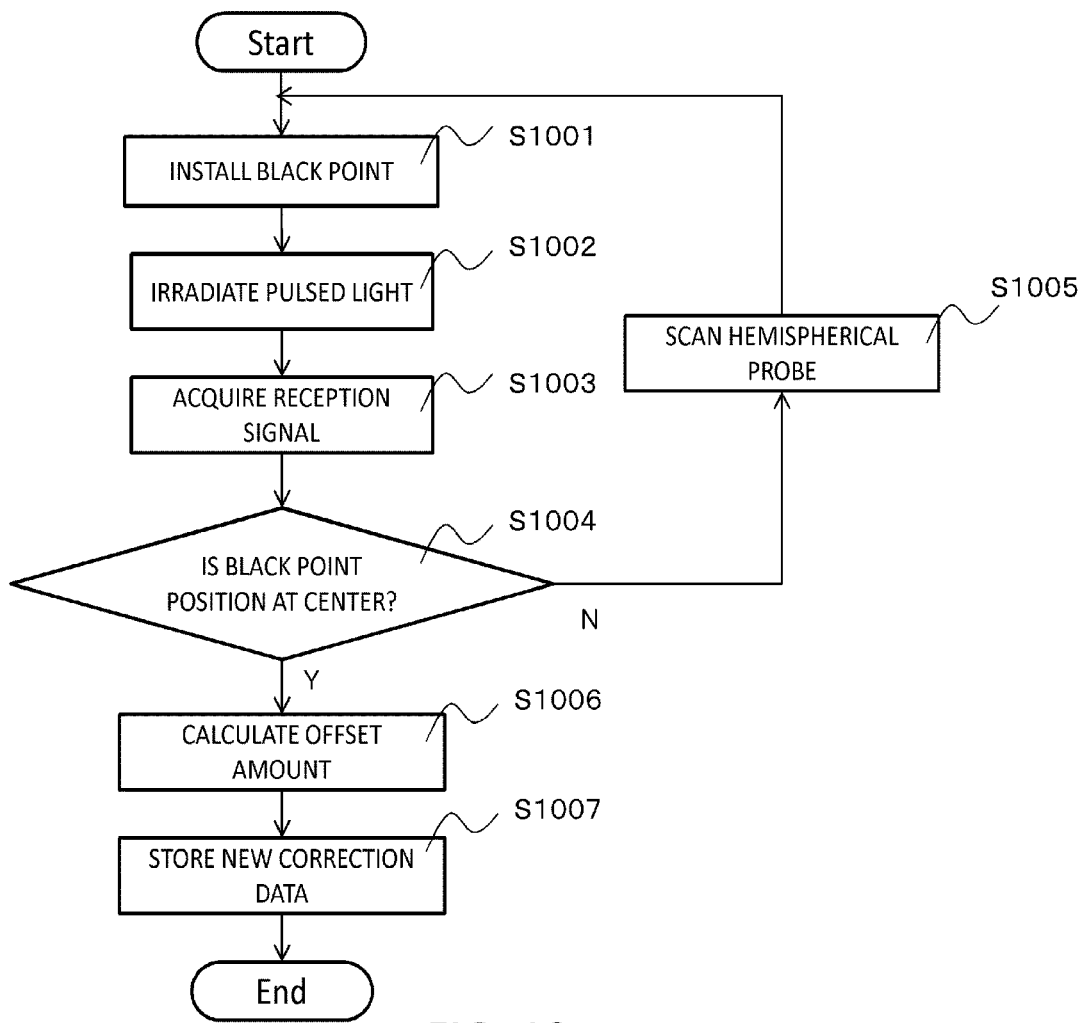
FIG. 10 is a flowchart illustrating a method of calculating correction data according to a third embodiment.

In FIG. 10 illustrating the process flow of the third embodiment, steps S1001 to S1005 are the same processes as those of FIG. 8. In the third embodiment, when the black point 52 is included in (matches) the central position in the determination flow of S1004, a variation in the amplitude of the reception signals is calculated in S1006, and new correction data is stored in S1007.

Hereinafter, calculation of the variation will be described in detail. When the black point 52 is present at the central position of the hemispherical probe 7, the amplitude of the reception signal (or the reception signal to which the correction data is applied) obtained in S1003 will be approximately the same for all elements. However, the element sensitivity decreases due to aging of the piezoelectric element, the strength of the reception signal of the element decreases and the amplitude may vary from element to element.

Thus, in the third embodiment, an offset amount indicating the difference from the correction data in the initial calibration is calculated for the offset amount of the amplitude as well as the phase time in S1006. The memory stores the data as new correction data in S1007. The image processor applies an appropriate gain to the strength of the reception signals of the respective elements so as to correct the variation in the amplitude by referring to the memory when reconstructing the image of the high-resolution region.

As described above, in the present embodiment, a method of correcting the reception signal during image reconstruction by calculating the new correction data based on the signal strength (amplitude) from the respective elements has been described.

As described in the respective embodiments, the object information acquiring apparatus of the present invention can arbitrarily adjust the relative position of the hemispherical probe to the black point fixed temporarily when performing calibration during a maintenance operation. Moreover, by performing an operation based on the reconstructed image and the reception signals obtained from the black point by photoacoustic measurement, it is possible to acquire correction data corresponding to the actual apparatus state and to use the correction data in image reconstruction.

Preferred Embodiments

Next, a preferred embodiment of the object information acquiring apparatus according to the present invention will be described. In FIG. 2, the object 21 is provided in the acoustic matching liquid 23. Here, it is preferable to provide a holding member for holding the object in that the holding member fixes the shape of the object to suppress a movement of the object. As a material of the holding member, a cup- or bowl-shaped material which transmits light and acoustic waves is preferred. An acoustic matching material may preferably provided between the object and the inner side of the holding member.

A support having a shape other than the hemispherical shape may be used as the support of the probe. For example, the present invention can be applied to a shape obtained by cutting a portion of a sphere along a plane such as a spherical crown or band shape approximately similarly to the hemispherical shape. That is, when the high-resolution region is set at the center of a sphere including a spherical crown or band, the correction data of the respective elements can be treated similarly to the case of a hemisphere.

Moreover, even when the shape of the support is not a portion of a sphere, the present invention can be applied to such a shape that can hold a plurality of elements so that the high sensitivity directions (directivity axes) of at least some elements converge. In this case, a region at which the directivity axes of the plurality of elements cross is set as the high-resolution region. Since the distance from the high-resolution region to each element is determined based on the apparatus design, the arrival time of acoustic waves from the black point to the element can be acquired by computing the time based on the acoustic velocity in the path from the high-resolution region to each element. Moreover, the attenuation of acoustic waves can be acquired by computation. Thus, the correction data for calibration including the information based on distance and the information based on the reception sensitivity can be created by taking the difference in the distance from the high-resolution region to each element into consideration. Moreover, by applying the methods of the respective embodiments, it is possible to update the correction data or create revision data for the correction data. Examples of the shape of the support include a curved surface shape such as a dish shape, a box shape, a shape obtained by cutting a portion of an ellipse, and a shape obtained by combining a plurality of planar surfaces and curved surfaces.

The black point which is a light absorber for calibration is preferably formed of a material having a high absorption coefficient. For example, a member obtained by solidifying carbon in a spherical form or a cubic form can be preferably used as the black point. The size of the black point can be arbitrarily set depending on the resolution of the apparatus and the like, and for example, the diameter or each side thereof is 0.5 mm to 1 mm. Moreover, a material that simulates a light absorber serving as a measurement target and a material having an absorption coefficient ideal for the wavelength of light used for measurement can be used. Further, a plurality of light absorbers may be disposed as necessary, which, however, makes computation complex.

Although the piezoelectric element is ideally used as the acoustic detecting element, the present invention is not limited thereto. Other conversion elements may be used in the present invention because these elements have a more or less problem of a decrease in the installing accuracy and the reception sensitivity.

Various methods such as two-dimensional scanning in the XY-directions, three-dimensional scanning including the Z-direction, and spiral scanning can be used for the scanning by the scanning controller and the scanning mechanism unit in the present invention. The probe itself can be controlled to rotate about the Z-direction. Moreover, photoacoustic waves may be acquired while moving the probe continuously and a step-and-repeat method of alternately repeating information acquisition and scanning may be performed. Various existing image reconstruction methods such as the Fourier transform method and a phasing addition method as well as back-projection can be used. The receiver performs a process of converting analog electrical signals to digital electrical signals, a process of amplifying the signal strength, and various correction processes. The strength correction performed using the correction data of the present invention may be performed together with the amplification process and may be performed separately by the image processor.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-213117, filed on Oct. 17, 2014, which is hereby incorporated by reference herein in its entirety.

What is claimed is:

1. An object information acquiring apparatus comprising:
a processor configured to acquire information about the inside of an object using electrical signals output from a plurality of detecting elements supported by a probe so that a high-resolution region in which directivity axes of at least part of the plurality of detecting elements converge is formed, wherein the electrical signals being signals obtained in response to a reception of an acoustic wave propagated from the object irradiated with light; and
a memory configured to store correction data for correcting the electrical signals output by the plurality of detecting elements, and used when the processor acquires the information about the inside of the object, the correction data including information based on a position of each of the plurality of detecting elements and information based on sensitivity, wherein
the processor revises the correction data on the basis of the electrical signals output by the plurality of detecting elements when a light absorber for calibration disposed at a predetermined position in relation to the probe is used as the object during calibration of the object information acquiring apparatus.

2. The object information acquiring apparatus according to claim 1, wherein the predetermined position at which the light absorber for calibration is disposed is a position set as the high-resolution region according to design of the object information acquiring apparatus and the probe.

3. The object information acquiring apparatus according to claim 1, wherein the correction data is data for correcting the electrical signals, which are output from the plurality of detecting elements, so as to have such a phase and a strength that the electrical signals are to have, when the light absorber for calibration is disposed in the high-resolution region.

4. The object information acquiring apparatus according to claim 1, wherein the information on the position included in the correction data is a distance between the high-resolution region and each of the plurality of detecting elements.

5. The object information acquiring apparatus according to claim 1, wherein the information based on the position included in the correction data is an arrival time of the acoustic wave from the high-resolution region to each of the plurality of detecting elements.

6. The object information acquiring apparatus according to claim 1, wherein the information based on the sensitivity included in the correction data is information indicating strength of the electrical signal relative to strength of the acoustic wave received by the detecting element.

7. The object information acquiring apparatus according to claim 1, wherein the information based on the sensitivity included in the correction data is information indicating a gain to be applied to the electrical signal output by each of the plurality of detecting elements.

8. The object information acquiring apparatus according to claim 1, wherein
a relative position of the probe to the light absorber for calibration can be changed, and
the processor changes the relative position to be in a second relation when the information about the inside of the object, acquired when the relative position is in a first relation, is not in a predetermined range indicating that the light absorber for calibration is included in the high-resolution region.

9. The object information acquiring apparatus according to claim 1, wherein
a relative position of the probe to the light absorber for calibration can be changed,
the plurality of detecting elements each acquire the electrical signal originating from the light absorber for calibration at a plurality of positions, and
the processor calculates the relative position on the basis of the electrical signals acquired at the plurality of positions so that the light absorber for calibration is included in the high-resolution region.

10. The object information acquiring apparatus according to claim 8, further comprising:
    a scanner configured to move the probe.

11. The object information acquiring apparatus according to claim 1, further comprising:
    a fixing member configured to dispose the light absorber for calibration in the high-resolution region.

12. The object information acquiring apparatus according to claim 11, wherein the fixing member is a cup.

13. The object information acquiring apparatus according to claim 1, wherein the memory revises the correction data by rewriting the correction data during the calibration.

14. The object information acquiring apparatus according to claim 1, wherein the memory stores revision data for the correction data during the calibration.

15. An object information acquiring apparatus comprising:
    a controller configured to control a movement of an acoustic probe supporting a plurality of detecting elements so that a region in which directivity axes of at least part of the plurality of detecting elements converge is formed; and
    a memory configured to store correction data for correcting electrical signals output by the plurality of detecting elements, the correction data including information based on a position of each of the plurality of detecting elements and information based on sensitivity,
    wherein the controller controls, in a calibration mode, the acoustic probe to move with respect to a light absorber so that the light absorber lies within the region.

16. The object information acquiring apparatus according to claim 15, wherein the correction data is data for correcting the electrical signals, which are output from the plurality of detecting elements, so as to have such a phase and a strength that the electrical signals are to have, when the light absorber for calibration is disposed in the region.

17. The object information acquiring apparatus according to claim 15, wherein the information based on the position included in the correction data is an arrival time of the acoustic wave from the region to each of the plurality of detecting elements.

18. The object information acquiring apparatus according to claim 15, wherein the information based on the position included in the correction data is an arrival time of the acoustic wave from the region to each of the plurality of detecting elements.

19. The object information acquiring apparatus according to claim 15, wherein the information based on the sensitivity included in the correction data is information indicating strength of the electrical signal relative to strength of the acoustic wave received by the detecting element.

20. The object information acquiring apparatus according to claim 15, wherein the information based on the sensitivity included in the correction data is information indicating a gain to be applied to the electrical signal output by each of the plurality of detecting elements.

21. The object information acquiring apparatus according to claim 15, wherein the memory revises the correction data by rewriting the correction data during an operation in the calibration mode.

22. The object information acquiring apparatus according to claim 15, wherein the memory stores revision data for the correction data during the calibration.

23. The object information acquiring apparatus according to claim 15, further comprising:
    a processor configured to acquire information about the inside of an object using electrical signals output from the plurality of detecting elements, wherein the electrical signals are signals obtained in response to a reception of an acoustic wave propagated from the object irradiated with light.

24. The object information acquiring apparatus according to claim 23, wherein the object is the light absorber, and
    wherein the processor revises the correction data on the basis of the electric signals output from the plurality of detecting elements, which received an acoustic wave generated in response to an irradiation of light onto the light absorber.

* * * * *